United States Patent [19]

Bub

[11] 4,108,852
[45] Aug. 22, 1978

[54] PROCESS FOR PREPARING 1,5-BENZODIAZEPINE-2-ONES

[75] Inventor: Oskar Bub, Ludwigshafen am Rhein, Fed. Rep. of Germany

[73] Assignee: Knoll AG., Ludwigshafen am Rhein, Fed. Rep. of Germany

[21] Appl. No.: 765,696

[22] Filed: Feb. 4, 1977

Related U.S. Application Data

[63] Continuation of Ser. No. 20,413, Mar. 17, 1970, abandoned.

[30] Foreign Application Priority Data

Mar. 18, 1969 [DE] Fed. Rep. of Germany ....... 1913536
Oct. 24, 1969 [DE] Fed. Rep. of Germany ....... 1953647

[51] Int. Cl.² .......................................... C07D 243/12
[52] U.S. Cl. .............................. 260/239.3 B; 424/244
[58] Field of Search ................................. 260/239.3 B

[56] References Cited

U.S. PATENT DOCUMENTS

| 3,321,468 | 5/1967 | Krapcho et al. | 260/239.3 B |
| 3,816,409 | 6/1974 | Bauer et al. | 260/239.3 B |

FOREIGN PATENT DOCUMENTS

| 18,752/65 | 8/1965 | Japan | 260/239.3 B |

OTHER PUBLICATIONS

Nicolaus et al., "Helv Chim. Acta", vol. 48, No. 8, pp. 1867-1885, (1965).
Ittyerah et al., "J. Chem. Soc.", (1958), pp. 467-480.
Testa et al., "Leibigs Annalen", Band 673, pp. 71-73, (1964).

*Primary Examiner*—Henry R. Jiles
*Assistant Examiner*—Robert T. Bond
*Attorney, Agent, or Firm*—Curtis, Morris & Safford

[57] ABSTRACT

1-Aryl-2,3,4,5-tetrahydro-1H-1,5-benzodiazepin-2-ones of the general formula

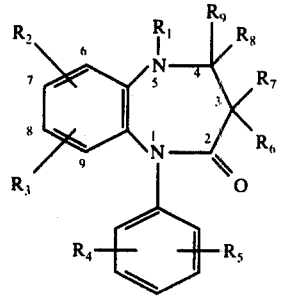

wherein:
$R_1$ is hydrogen, or unsaturated lower alkyl, preferably of 1-3 carbons, or unsaturated lower alkyl preferably of 2 - 3 carbons
$R_2$, $R_3$, $R_4$, $R_5$ are the same or different and are each hydrogen, halogen, lower alkyl, preferably methyl, lower alkoxy, preferably methoxy, or trifluromethyl, and
$R_6$, $R_7$, $R_8$, $R_9$ are the same or different and are each hydrogen or lower alkyl, preferably methyl.

The compounds are prepared by dehydrohalogenating substituted 2-(3'-halogenopropionylamino)-diphenyl amines of the general formula

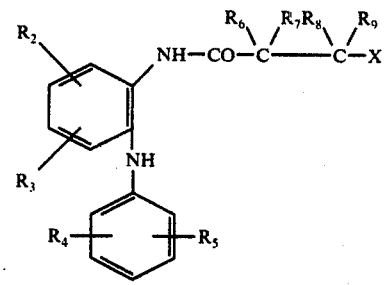

wherein $R_2$ to $R_9$ are the same as defined above and X is halogen, in the presence of a solvent and a base, to cyclize the amines and then alkylating to introduce the unsaturated lower alkyl radical $R_1$ on the nitrogen in the 5 position, if necessary. The compounds possess anticonvulsant, sedative and muscle relaxant properties.

4 Claims, No Drawings

PROCESS FOR PREPARING 1,5-BENZODIAZEPINE-2-ONES

This is a continuation, of application Ser. No. 20413 filed Mar. 17, 1970, now abandoned.

This invention relates to 1-aryl-2,3,4,5-tetrahydro-1H-1,5-benzodiazepin-2-ones and a process of preparing the same. The compounds possess valuable pharmacological properties particularly as anticonvulsants, sedatives and muscle relaxants.

The preparation of the compound 3,3-diethyl-1-phenyl-2,3,4,5-tetrahydro-1H-1,5-benzodiazepin-2-one by treating 1-(o-anilinophenyl)-3,3-diethyl azetidin-2-one with dilute acids is disclosed in Helv. Chim. Act. 48:1867, 1965 by B. J. R. Nicolaus et al. See also Chemical Reviews, 68, 747.

The primary object of the invention is the provision of new 1-aryl derivatives of 2,3,4,5-tetrahydro-1H-1,5-benzodiazepin-2-one and a new and improved process of preparing them.

The 1-aryl-2,3,4,5-tetrahydro-1H-1,5-benzodiazepin-2-ones compounds of the present invention are of the general formula

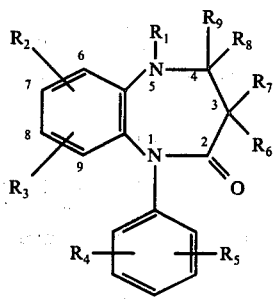

I.

wherein:
- $R_1$ is hydrogen, lower alkyl, preferably of 1-3 carbons, or unsaturated lower alkyl, preferably of 2-3 carbons
- $R_2$, $R_3$, $R_4$, $R_5$ are the same or different and are each hydrogen, halogen, preferably chlorine, lower alkyl, preferably methyl, lower alkoxy, preferably methoxy, or trifluoromethyl, and
- $R_6$, $R_7$, $R_8$, $R_9$ are the same or different and are each hydrogen or lower alkyl, preferably methyl.

In general, the process of the present invention comprises cyclizing substituted 2-(3'-halogeno-propionylamino)-diphenyl amine of the general formula

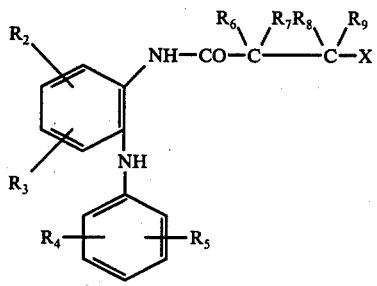

II.

wherein $R_2$, $R_3$, $R_4$, $R_5$, $R_6$, $R_7$, $R_8$ and $R_9$ are as defined above and X is halogen by cleaving hydrogen halide therefrom, preferably in the presence of a solvent and a base, and then introducing the radical $R_1$, if it is other than hydrogen, at the nitrogen in the 5 position by alkylation.

Since the cyclization reaction occurs by the removal of the hydrogen halide it is preferred that the reaction be carried out in the presence of a polar solvent, such as dimethyl formamide, and a base, such as the alkali carbonates or bicarbonates, or sodium amide. It will of course be understood that other solvents and bases can be used.

The cyclization reaction can be carried out at temperatures up to about 200° C. It can also be carried out at very low temperatures as with sodium amide in liquid ammonia. Compounds in which one or more of the substituents $R_2$, $R_3$, $R_4$ or $R_5$ is halogen can be prepared in an especially simple manner by simply heating corresponding compounds of the general formula II in dimethylformamide to about 100° to 150° C in the presence of potassium carbonate, the reaction being completed in about 2 hours.

The subsequent alkylation at the nitrogen atom in the 5 position can be accomplished in a conventional manner. Thus the cyclized compound may be reacted with alkylhalogenides or dialkylsulfates, preferably in the presence of acid-binding agents, or by reductive alkylation with carbonyl compounds in the presence of a reducing agent, such as catalytically energized hydrogen.

It is to be noted that the reaction is surprising since one would expect the cyclization of substituted 2-(3'-halogenopropionylamino)-diphenylamines to produce derivatives of 1-aryl-2,3,4,5-tetrahydro-1H-1,5-benzodiazepin-4-ones, and not compounds in which the oxygen is in the 2 position, i.e. the 2-one compounds of the present invention.

The following are illustrative but non-limitative examples of the invention.

EXAMPLE 1

1-Phenyl-2,3,4,5-tetrahydro-1H-1,5-benzodiazepin-2-one

A solution of 125 g 2-(3'-chloropropionylamino)-diphenylamine in 300 ml dimethylformamide is dropped into a boiling suspension of 65 g powdered anhydrous potassium carbonate in 300 ml dimethylformamide under vigorous agitation over a period of about ½ hour. Refluxing is continued for 2 hours. After cooling, the inorganic salt mixture is removed by filtration under suction and the solvent is distilled off from the filtrate under vacuum. The residue is dissolved in 500 ml chloroform, washed twice with water, and the solution is then dried over sodium sulfate. After distilling off the solvent, the crystalline residue is recrystallized from 500 ml acetic acid ethyl ester. The yield was 82 g of the compound having an m.p. = 170°–171° C (76% of the theory).

The 2-(3'-chloropropionylamino)-diphenylamine (m.p. = 115°–116° C, from isopropyl alcohol) used as a starting material is obtained by the interaction of 2-amino-diphenylamine with 3-chloropropionyl chloride.

EXAMPLE 2

The reaction of Example 1 is carried out using 2-(3'-bromopropionylamino)-diphenylamine (m.p. = 129°–130° C from isopropyl alcohol) as the starting material and it can be prepared in the same manner as 2-(3'-chloropropionylamino)-diphenylamine.

EXAMPLE 3

8-Chloro-1-phenyl-2,3,4,5-tetrahydro-1H-1,5-benzodiazepin-2-one having an m.p. = 179°–180° C (from alcohol) is prepared in the same manner as Example 1.

EXAMPLE 4

1-(4'-Chloro-phenyl)-2,3,4,5-tetrahydro-1H-1,5-benzodiazepin-2-one having an m.p. = 233°–234° C (from dimethylformamide) is prepared in the same manner as Example 1.

EXAMPLE 5

1-(4'-Chloro-phenyl)-8-chloro-2,3,4,5-tetrahydro-1H-1,5-benzodiazepin-2-one having an m.p. = 203°–204° C (from acetic ester) is prepared in the same manner as Example 1.

EXAMPLE 6

1-(2'-Chloro-phenyl)-2,3,4,5-tetrahydro-1H-1,5-benzodiazepin-2-one having an m.p. = 149°–150° C (from acetic ethyl ester) is prepared in the same manner as Example 1

EXAMPLE 7

1-(3'-Chloro-phenyl)-2,3,4,5-tetrahydro-1H-1,5-benzodiazepin-2-one having an m.p. = 183°–184° C (from isopropyl alcohol) is prepared in the same manner as Example 1.

EXAMPLE 8

1-(2'-Chloro-phenyl)-8-chloro-2,3,4,5-tetrahydro-1H-1,5-benzodiazepin-2-one having an m.p. = 188°–189° C (from isopropyl alcohol) is prepared in the same manner as Example 1.

EXAMPLE 9

7-Chloro-1-phenyl-2,3,4,5-tetrahydro-1H-1,5-benzodiazepin-2-one having an m.p. = 203°–204° C (from ethyl-methyl ketone) is prepared in the same manner as Example 1.

EXAMPLE 10

9-Chloro-1-phenyl-2,3,4,5-tetrahydro-1H-1,5-benzodiazepin-2-one having an m.p. = 213°–214° C (from acetic ethyl ester) is prepared in the same manner as Example 1.

EXAMPLE 11

9-Chloro-1-(2'-chloro-phenyl)-2,3,4,5-tetrahydro-1H-1,5-benzodiazepin-2-one having an m.p. = 212°–213° C (from ethanol) is prepared in the same manner as Example 1.

EXAMPLE 12

1-Phenyl-2,3,4,5-tetrahydro-1H-1,5-benzodiazepin-2-one 1.2 g sodium is dissolved in 300 ml liquid ammonia and upon the addition of a few granules of iron-(III)-nitrate, i.e. ferric nitrate, it is stirred at about −50° C for approximately 2 hours until the disappearance of the blue coloration. 13.7 g of 2-(3'-chloropropionylamino)-diphenyl amine is introduced in portions into the thus obtained sodium amide suspension. The reaction mixture is stirred still for one 1 hour at about −50° C, the cooling bath is removed, and the ammonia is allowed to evaporate with stirring. The residue is then taken up in chloroform and water, the chloroform solution is dried over sodium sulfate, and the solvent is distilled off. Upon recrystallization from acetic acid ethyl ester 10.2 g of colorless crystals are obtained whose m.p. = 170°–171° C (85% of the theory).

EXAMPLE 13

8-Chloro-5-methyl-1-phenyl-2,3,4,5-tetrahydro-1H-1,5-benzodiazepin-2-one 20.4 g 8-chloro-1-phenyl-2,3,4,5-tetrahydro-1H-1,5-benzodiazepin-2-one is stirred for 2 hours on a water bath with 12.8 g methyl iodide and 10 g anhydrous potassium carbonate. The inorganic material is removed by filtration under suction and the filtrate is diluted with 200 ml water. The crystalline precipitate is filtered under suction, washed with water, and recrystallized from alcohol. The yield is 20 g of the m.p. = 143°–144° C (93% of the theory).

EXAMPLE 14

5-Methyl-1-phenyl-2,3,4,5-tetrahydro-1H-1,5-benzodiazepin-2-one having an m.p. = 103°–104° C (from diisopropyl ether) is prepared in the same manner as Example 13.

EXAMPLE 15

5-Ethyl-1-phenyl-2,3,4,5-tetrahydro-1H-1,5-benzodiazepin-2-one having an m.p. = 92°–93° C (from diisopropyl ether) is prepared in the same manner as Example 13.

EXAMPLE 16

5-Ethyl-8-chloro-1-phenyl-2,3,4,5-tetrahydro-1H-1,5-benzodiazepin-2-one having an m.p. = 132°–133° C (from alcohol) is prepared in the same manner as Example 13.

EXAMPLE 17

5-Allyl-1-phenyl-2,3,4,5-tetrahydro-1H-1,5-benzodiazepin-2-one having an m.p. = 71°–72° C (from petroleum ether) is prepared in the same manner as Example 13.

EXAMPLE 18

5-Allyl-8-chloro-1-phenyl-2,3,4,5-tetrahydro-1H-1,5-benzodiazepin-2-one having an m.p. = 135°–136° C (from alcohol) is prepared in the same manner as Example 13.

EXAMPLE 19

1-(4'-Chloro-phenyl)-5-methyl-2,3,4,5-tetrahydro-1H-1,5-benzodiazepin-2-one having an m.p. = 89°–90° C (from diisopropyl ether) is prepared in the same manner as Example 13.

EXAMPLE 20

1-(2'-Chloro-phenyl)-5-methyl-2,3,4,5-tetrahydro-1H-1,5-benzodiazepin-2-one having an m.p. = 128°–129° C (from isopropyl alcohol) is prepared in the same manner as Example 13.

EXAMPLE 21

1-(3'-Chloro-phenyl)-5-methyl-2,3,4,5-tetrahydro-1H-1,5-benzodiazepin-2-one having an m.p. = 87° - 88° C (from diisopropyl ether) is prepared in the same manner as Example 13.

EXAMPLE 22

7-Chloro-5-methyl-1-phenyl-2,3,4,5-tetrahydro-1H-1,5-benzodiazepin-2-one having an m.p. = 105°–106° C (from diisopropyl ether) is prepared in the same manner as Example 13.

EXAMPLE 23

8-Chloro-1-(2'-chloro-phenyl)-5-methyl-2,3,4,5-tetrahydro-1H-1,5-benzodiazepin-2-one having an m.p. = 187° – 188° C (from isopropyl alcohol) is prepared in the same manner as Example 13.

EXAMPLE 24

8-Chloro-1-(4'-chloro-phenyl)-5-methyl-2,3,4,5-tetrahydro-1H-1,5-benzodiazepin-2-one having an m.p. = 135° – 136° C (from isopropyl alcohol) is prepared in the same manner as Example 13.

EXAMPLE 25

9-Chloro-5-methyl-1-phenyl-2,3,4,5-tetrahydro-1H-1,5-benzodiazepin-2-one having an m.p. = 160°–161° C (from isopropyl alcohol) is prepared in the same manner as Example 13.

EXAMPLE 26

9-Chloro-1-(2'-chloro-phenyl)-5-methyl-2,3,4,5-tetrahydro-1H-1,5-benzodiazepin-2-one having an m.p. = 175° – 176° C (from isopropyl alcohol) is prepared in the same manner as Example 13.

EXAMPLE 27

8-Chloro-4-methyl-1-phenyl-2,3,4,5-tetrahydro-1H-1,5-benzodiazepin-2-one

To a boiling suspension of 37 g powdered anhydrous potassium carbonate in 200 ml dimethylformamide a solution of 97 g 2-(3'-bromobutyrylamino)-5-chlorodiphenyl amine in 200 ml dimethylformamide is dropped over a period of about ½ hour and is subsequently refluxed for 2 hours. Upon cooling, the inorganic salt mixture is removed by filtration under suction and the solvent is distilled off completely in vacuum from the filtrate. The crystalline residue is washed with water and recrystallized from isopropanol. The yield is 59 g having an m.p. = 167°–168° C (78% of the theory).

2-(3'-bromobutyrylamino)-5-chloro-diphenylamine (m.p. = 171°–172° C, from ethanol) which is used as a starting material is obtained by the interaction of 2-amino-5-chloro-diphenyl amine with 3-bromo-butyryl chloride.

EXAMPLE 28

3-Methyl-1-phenyl-2,3,4,5-tetrahydro-1H-1,5-benzodiazepin-2-one

In 250 ml liquid ammonia are dissolved 1.2 g sodium and upon addition of some crystals of iron-(III)-nitrate, i.e. ferric nitrate, the mixture is stirred at about −50° C until disappearance of the blue coloration. Into the suspension of sodium amide formed 17 g 2-(3'-bromoisobutyrylamino)-diphenylamine is introduced in portions. The cooling bath is then removed and the ammonia is evaporated under stirring. The crystalline residue is washed with water and is recrystallized from acetic acid ethyl ester. The yield is 10.5 g having an m.p. = 146°–147° C (83% of the theory).

2-(3'-bromoisobutyrylamino)-diphenyl amine (m.p. = 98°–99° C from isopropyl alcohol) which is used as a starting material is obtained by the interaction of 2-aminodiphenyl amine with 3-bromo-isobutyryl chloride.

EXAMPLE 29

7-Chloro-3-methyl-1-phenyl-2,3,4,5-tetrahydro-1H-1,5-benzodiazepin-2-one having an m.p. = 172°–173° C (from acetic acid ethyl ester) is prepared in the same manner as Examples 27 and 28.

EXAMPLE 30

8-Chloro-3-methyl-1-phenyl-2,3,4,5-tetrahydro-1H-1,5-benzodiazepin-2-one having an m.p. = 128°–129° C (from isopropyl alcohol) is prepared in the same manner as Examples 27 and 28.

EXAMPLE 31

4-Methyl-1-phenyl-2,3,4,5-tetrahydro-1H-1,5-benzodiazepin-2-one having an m.p. = 130°–131° C (from acetic acid ethyl ester) is prepared in the same manner as Examples 27 and 28.

EXAMPLE 32

7-Chloro-4-methyl-1-phenyl-2,3,4,5-tetrahydro-1H,1,5-benzodiazepin-2-one having an m.p. = 170°–172° C (from ethanol) is prepared in the same manner as Examples 27 and 28.

EXAMPLE 33

4-Methyl-1-(4'-chlorophenyl)-2,3,4,5-tetrahydro-1H-1,5-benzodiazepin-2-one having an m.p. = 159°–160° C (from isopropyl alcohol) is prepared in the same manner as Examples 27 and 28.

EXAMPLE 34

3,3-Dimethyl-1-phenyl-2,3,4,5-tetrahydro-1H-1,5-benzodiazepin-2-one having an m.p. = 151°–152° C (from isopropyl alcohol) is prepared in the same manner as Examples 27 and 28.

EXAMPLE 35

8-Chloro-3,3-dimethyl-1-phenyl-2,3,4,5-tetrahydro-1H-1,5-benzodiazepin-2-one having an m.p. = 132°–133° C (from isopropyl alcohol) is prepared in the same manner as Examples 27 and 28.

EXAMPLE 36

3,4-Dimethyl-1-phenyl-2,3,4,5-tetrahydro-1H-1,5-benzodiazepin-2-one having an m.p. = 193°–194° C (from ethanol) is prepared in the same manner as Examples 27 and 28.

EXAMPLE 37

8-Chloro-3,4-dimethyl-1-phenyl-2,3,4,5-tetrahydro-1H, 1,5-benzodiazepin-2-one having an m.p. = 194°–195° C (from ethanol) is prepared in the same manner as Examples 27 and 28.

EXAMPLE 38

4,4-Dimethyl-1-phenyl-2,3,4,5-tetrahydro-1H,1,5-benzodiazepin-2-one having an m.p. = 146°–147° C (from diisopropyl ether) is prepared in the same manner as Examples 27 and 28.

EXAMPLE 39

3-Chloro-4,4-dimethyl-1-phenyl-2,3,4,5-tetrahydro-1H-1,5-benzodiazepin-2-one having an m.p. = 180°–181° C (from diisopropyl ether) is prepared in the same manner as Examples 27 and 28.

EXAMPLE 40

8-Chloro-4,5-dimethyl-1-phenyl-2,3,4,5-tetrahydro-1H-1,5-benzodiazepin-2-one 28.6 g 8-chloro-4-methyl-1-phenyl-2,3,4,5-tetrahydro-1H-1,5-benzodiazepin-2-one in 100 ml dimethylformamide is stirred with 18 g methyl iodide and 14 g anhydrous potassium carbonate for 2 hours on a boiling water bath. The reaction mixture is poured into 500 ml water and extracted with ether several times. The ethereal extracts are washed with water and dried over sodium sulfate. Upon distilling off the solvent, the crystalline residue is recrystallized from acetic acid ethyl ester. The yield is 24.5 g having an m.p. = 113°–114° C (82% of the theory).

EXAMPLE 41

3,5-Dimethyl-1-phenyl-2,3,4,5-tetrahydro-1H-1,5-benzodiazepin-2-one having an m.p. = 101°–102° C (from diisopropyl-ether) is prepared in the same manner as Example 40.

EXAMPLE 42

7-Chloro-3,5-dimethyl-1-phenyl-2,3,4,5-tetrahydro-1H-1,5-benzodiazepin-2-one having an m.p. = 116°–117° C (from isopropyl alcohol) is prepared in the same manner as Example 40.

EXAMPLE 43

8-Chloro-3,5-dimethyl-1-phenyl-2,3,4,5-tetrahydro-1H-1,5-benzodiazepin-2-one having an m.p. = 151°–152° C (from isopropyl alcohol) is prepared in the same manner as Example 40.

EXAMPLE 44

4,5-Dimethyl-1-phenyl-2,3,4,5-tetrahydro-1H-1,5-benzodiazepin-2-one having an m.p. = 97°–98° C (from dimethyl ether) is prepared in the same manner as Example 40.

EXAMPLE 45

7-Chloro-4,5-dimethyl-1-phenyl-2,3,4,5-tetrahydro-1H-1,5-benzodiazepin-2-one having an m.p. = 122°–123° C (from diisopropyl ether) is prepared in the same manner as Example 40.

EXAMPLE 46

8-Chloro-3,3,5-trimethyl-1-phenyl-2,3,4,5-tetrahydro-1H-1,5-benzodiazepin-2-one having an m.p. = 191°–192° C (from isopropyl alcohol) is prepared in the same manner as Example 40.

EXAMPLE 47

8-Chloro-3,4,5-trimethyl-1-phenyl-2,3,4,5-tetrahydro-1H-1,5-benzodiazepin-2-one having an m.p. = 116°–117° C (from isopropyl alcohol) is prepared in the same manner as Example 40.

EXAMPLE 48

5-Allyl-4-methyl-1-phenyl-2,3,4,5-tetrahydro-1H-1,5-benzodiazepin-2-one having an m.p. = 108°–109° C (from isopropyl alcohol) is prepared in the same manner as Example 40.

EXAMPLE 49

1-(4'-Chlorophenyl)-4,5-dimethyl-2,3,4,5-tetrahydro-1H-1,5-benzodiazepin-2-one having an m.p. = 80°–82° C (from petroleum ether) is prepared in the same manner as Example 40.

EXAMPLE 50

8-Chloro-1-(4'-methoxyphenyl)-2,3,4,5-tetrahydro-1H-1,5-benzodiazepin-2-one

To a boiling suspension of 28 g anhydrous potassium carbonate in 150 ml dimethylformamide a solution of 68 g 2-(3-chloropropionylamino)-5-chloro-4'-methoxy-diphenyl amine in 150 ml dimethylformamide is dropped under stirring over a period of about ½ hour and, subsequently, the mixture is refluxed for 2 hours. Upon cooling, the inorganic salt mixture is filtered off by suction and the filtrate is rewashed with dimethylformamide; then the entire solvent is distilled off under vacuum. The crystalline residue is washed with water and recrystallized from ethanol. The yield is 44 g having an m.p. = 198°–199° C (73% of the theory).

2-(3-chloropropionylamino)-5-chloro-4'-methoxy diphenyl amine m.p. = 131°–132° C (from isopropyl alcohol) which is used as a starting material is obtained by the interaction of 2-amino-5-chloro-4'-methoxy-diphenyl amine with 3-chloropropionyl chloride.

EXAMPLE 51

1-(4'-methylphenyl)-2,3,4,5-tetrahydro-1H-1,5-benzodiazepin-2-one

In 500 ml liquid ammonia 2.4 g sodium is dissolved and a few granules of iron-(III)-nitrate, i.e. ferric nitrate, are added. The mixture is stirred at about −50° C until the disappearance of the blue coloration. 29 g 2-(3-chloropropionylamino)-4'-methyl-diphenyl amine is introduced in portions into the suspension of sodium amide so obtained. The cooling bath is then removed and the ammonia is evaporated under stirring. The crystalline residue is washed with water and recrystallized from isopropyl alcohol. The yield is 20.5 g having an m.p. = 198°–199° C (81% of the theory).

2-(3-chloropropionylamino)-4'-methyl-diphenyl amine of the m.p. = 112°–113° C (from isopropyl alcohol) which is used as a starting material is obtained by the interaction of 2-amino-4'-methyl-diphenyl amine with 3-chloro-propionyl chloride.

EXAMPLE 52

8-Chloro-1-(2'-methylphenyl)-2,3,4,5-tetrahydro-1H-1,5-benzodiazepin-2-one having an m.p. = 150°–151° C (from isopropyl alcohol) is prepared in the same manner as Example 51.

EXAMPLE 53

1-(2'-methoxyphenyl)-2,3,4,5-tetrahydro-1H-1,5-benzodiazepin-2-one having an m.p. = 127°–128° C (from acetic acid ethyl ester) is prepared in the same manner as Example 51.

EXAMPLE 54

8-Chloro-1-(2'-methoxyphenyl)-2,3,4,5-tetrahydro-1H-1,5-benzodiazepin-2-one having an m.p. = 147°–148° C (from acetic acid ethyl ester) is prepared in the same manner as Example 51.

EXAMPLE 55

1-(4'-methoxyphenyl)-2,3,4,5-tetrahydro-1H-1,5-benzodiazepin-2-one having an m.p. = 188°–189° C (from ethanol) is prepared in the same manner as Example 51.

EXAMPLE 56

8-Chloro-1-(2'-fluorophenyl)-2,3,4,5-tetrahydro-1H-1,5-benzodiazepin-2-one having an m.p. = 168°–169° C (from isopropyl alcohol) is prepared in the same manner as Example 51.

EXAMPLE 57

1-(3'-Trifluoromethylphenyl)-2,3,4,5-tetrahydro-1H-1,5-benzodiazepin-2-one having an m.p. = 147°–148° C (from diisopropyl ether) is prepared in the same manner as Example 51.

EXAMPLE 58

3-Methyl-1-(3'trifluoromethylphenyl)-2,3,4,5-tetrahydro-1H-1,5-benzodiazepin-2-one having an m.p. = 168°–169° C (from isopropyl alcohol) is prepared in the same manner as Example 51.

EXAMPLE 59

8-Chloro-1-(3'-methylphenyl)-2,3,4,5-tetrahydro-1H-1,5-benzodiazepin-2-one having an m.p. = 172°–173° C (from ethanol) is prepared in the same manner as Example 51.

EXAMPLE 60

8-Chloro-1-(4'-methylphenyl)-2,3,4,5-tetrahydro-1H-1,5-benzodiaxepin-2-one having an m.p. = 208°–209° C (from ethyl methyl ketone) is prepared in the same manner as Example 51.

EXAMPLE 61

8-Chloro-1-(3'-methoxyphenyl)-2,3,4,5-tetrahydro-1H-1,5-benzodiazepin-2-one having an m.p. = 178°–179° C is prepared in the same manner as Example 51.

EXAMPLE 62

8-Chloro-1-(4'-bromophenyl)-2,3,4,5-tetrahydro-1H-1,5-benzodiazepin-2-one having an m.p. = 216°–217° C (from ethyl methyl ketone) is prepared in the same manner as Example 51.

EXAMPLE 63

8-Chloro-1-(3'-trifluoromethylphenyl)-2,3,4,5-tetrahydro-1H-1,5-benzodiazepin-2-one having an m.p. = 148°–149° C (from diisopropyl ether) is prepared in the same manner as Example 51.

EXAMPLE 64

1-(2',5'-Dichlorophenyl)-2,3,4,5-tetrahydro-1H-1,5-benzodiazepin-2-one having an m.p. = 197°–198° C (from acetic acid ethyl ester) is prepared in the same manner as Example 51.

EXAMPLE 65

1-(2',6'-Dichlorophenyl)-2,3,4,5-tetrahydro-1H-1,5-benzodiazepin-2-one having an m.p. = 211°–212° C (from chloroform) is prepared in the same manner as Example 51.

EXAMPLE 66

7-Methyl-1-phenyl-2,3,4,5-tetrahydro-1H-1,5-benzodiazepin-2-one having an m.p. = 164°–165° C (from acetic acid ethyl ester) is prepared in the same manner as Example 51.

EXAMPLE 67

7-Methoxy-1-phenyl-2,3,4,5-tetrahydro-1H-1,5-benzodiazepin-2-one having an m.p. = 216°–217° C (from glacial acetic acid) is prepared in the same manner as Example 51.

EXAMPLE 68

7,8-Dichloro-1-phenyl-2,3,4,5-tetrahydro-1H-1,5-benzodiazepin-2-one having an m.p. = 193°–194° C (from methanol) is prepared in the same manner as Example 51.

EXAMPLE 69

1-Phenyl-7-trifluoromethyl-2,3,4,5-tetrahydro-1H-1,5-benzodiazepin-2-one having an m.p. = 168°–169° C (from acetic acid ethyl ester/petroleum ether) is prepared in the same manner as Example 51.

EXAMPLE 70

1-(2'-Chlorophenyl)-7-trifluoromethyl-2,3,4,5-tetrahydro-1H-1,5-benzodiazepin-2-one having an m.p. = 176°–177° C (from isopropyl alcohol) is prepared in the same manner as Example 51.

EXAMPLE 71

8-Chloro-1-(4'-methoxyphenyl)-5-methyl-2,3,4,5-tetrahydro-1H-1,5-benzodiazepin-2-one 23 g 8-chloro-1-(4'-methoxyphenyl)-2,3,4,5-tetrahydro-1H-1,5-benzodiazepin-2-one is stirred in 150 ml dimethylformamide for about 2 hours on a boiling water bath to which has been added 15 g methyl iodide and 11 g anhydrous potassium carbonate. The reaction mixture is poured into 1 liter water whereby the product is thoroughly crystallized with stirring. The reaction mixture is filtered by suction, washed thoroughly with water, and crystallized from isopropyl alcohol. The yield is 19 g having an m.p. = 144°–145° C (79% of the theory).

EXAMPLE 72

8-Chloro-5-methyl-1-(2'-methylphenyl)-2,3,4,5-tetrahydro-1H-1,5-benzodiazepin-2-one having an m.p. = 148°–149° C (from isopropyl alcohol) is prepared in the same manner as Example 71.

EXAMPLE 73

1-(2'-Methoxyphenyl)-5-methyl-2,3,4,5-tetrahydro-1H-1,5-benzodiazepin-2-one having an m.p. = 129°–130° C (from acetic acid ethyl ester) is prepared in the same manner as Example 71.

EXAMPLE 74

8-Chloro-1-(2'-methoxyphenyl)-5-methyl-2,3,4,5-tetrahydro-1H-1,5-benzodiazepin-2-one having an m.p. = 150°–151° C (from acetic acid ethyl ester/petroleum ether) is prepared in the same manner as Example 71.

EXAMPLE 75

8-Chloro-5-methyl-1-(3'-methylphenyl)-2,3,4,5-tetrahydro-1H-1,5-benzodiazepin-2-one having an m.p. = 135°–136° C (from isopropyl alcohol) is prepared in the same manner as Example 71.

EXAMPLE 76

8-Chloro-5-methyl-1-(2'-fluorophenyl)-2,3,4,5-tetrahydro-1H-1,5-benzodiazepin-2-one having an m.p. =

116°–117° C (from 50% ethanol) is prepared in the same manner as Example 71.

EXAMPLE 77

1-(4'-Methoxyphenyl)-5-methyl-2,3,4,5-tetrahydro-1H, 1,5-benzodiazepin-2-one having an m.p. = 78°–79° C (from diisopropyl ether) is prepared in the same manner as Example 71.

EXAMPLE 78

5-Allyl-1-(4'-methoxyphenyl)-2,3,4,5-tetrahydro-1H-1,5-benzodiazepin-2-one having an b.p.$_{0.1\ mm}$ = 189°–192° C is prepared in the same manner as Example 71.

EXAMPLE 79

5-Methyl-1-(3'-trifluoromethylphenyl)-2,3,4,5-tetrahydro-1H-1,5-benzodiazepin-2-one having an m.p. = 104°–105° C (from diisopropyl ether) is prepared in the same manner as Example 71.

EXAMPLE 80

1-(2',3'-Dichlorophenyl)-5-methyl-2,3,4,5-tetrahydro-1H-1,5-benzodiazepin-2-one having an m.p. = 134°–135° C (from isorpopyl alcohol) is prepared in the same manner as Example 71.

EXAMPLE 81

1-(2',5-Dichlorophenyl)-5-methyl-2,3,4,5-tetrahydro-1H-1,5-benzodiazepin-2-one having an m.p. = 133°–134° C (from isopropyl alcohol) is prepared in the same manner as Example 71.

EXAMPLE 82

7,8-Dichloro-5-methyl-1-phenyl-2,3,4,5-tetrahydro-1H-1,5-benzodiazepin-2-one having an m.p. = 109°–110° C (from isopropyl alcohol) is prepared in the same manner as Example 71.

EXAMPLE 83

1-Phenyl-2,3,4,5-tetrahydro-1H-1,5-benzodiazepin-2-one 9.2 g of 2-amino-diphenylamine and 4.5 g acrylic acid in 20 ml of 5N sulfuric acid are heated under reflux for 3 hours. After completion of the reaction, the reaction mixture is made alkaline by the addition of concentrated aqueous ammonia solution. The oily reaction product is extracted with chloroform and the chloroform solution is washed with water, dried over sodium sulfate and the solution is distilled off. The residue is recrystallized from isopropyl alcohol. The yield is 1.2 g having an m.p. = 169°–170° C (10% of the theory).

It should be noted further that the compounds of the invention wherein $R_2$, $R_3$, $R_4$ and $R_5$ are halogen are preferably prepared at low temperatures as, for example, with sodium amide in liquid ammonia.

The compounds of the invention are preferably administered orally in the form of tablets, capsules and dragees but can be administered in other suitable forms. They are preferably diluted with suitable diluting agents, thus, allowing better and more economical use to be made thereof.

As solid carriers, which are suitable for the manufacture of useful pharmaceutical preparations, various inert pulverulent distributing agents as they are conventionally used in pharmaceutical compounding may be employed.

When preparing tablets, capsules, dragees and the like, the commonly used diluting agents, binders, lubricants, and the like are added, such as sugar, lactose, talcum, starch, pectins; as binders gelatin, gum arabic, methyl cellulose, yeast extract, agar, tragacanth, and as lubricating agents magnesium stearate, stearic acid, and others.

The compounds of the invention are useful for the treatment of anxiety, for skeletal muscle relaxation and for combating alcoholism. A daily therapeutic dosage can be maintained by administering 10 to 100 mg of the compound in suitable dosage units as, for example, 2, 5, 10, 25 and 50 mg per tablet, capsule or dragee. The daily dosage must be adjusted to the individual needs for the patient. For ordinary anxiety a daily dosage of 10–30 mg is preferred while 100 mg per day may be required for more severely disturbed patients.

The activities of the new compounds were determined in the following tests:

1. The acute toxity was determined according to J. F. Litchfield, F. Wilcoxon, J. Pharmacol. and Exp. Therap. 96, 99 - 113 (1949).
2. The sedative activity was determined according to J. Stewart, Am. J. Physiol. 1, 40 (1898).
3. The anticonvulsant activity was determined according to the methods introduced by C. S. Goodman et al. Arch. int. Pharmacodyn 78, 144 - 162 (1949) and by C. S. Goodman et al. J. Pharm. exp. Ther. 108, 168 - 176 (1953).

In all tests the new compounds showed much better results than meprobamat.

What is claimed is:

1. The method of making a 1-aryl-2,3,4,5-tetrahydro-1H-1,5-benzodiazepin-2-one of the formula

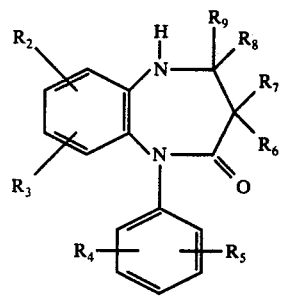

wherein $R_2$, $R_3$, $R_4$, and $R_5$ are the same or different and are each hydrogen, lower alkyl, lower alkoxy, or trifluoromethyl; and $R_6$, $R_7$, $R_8$, and $R_9$ are the same or different and are each hydrogen or lower alkyl, which method comprises reacting a substituted 2-diphenyl amine of the formula

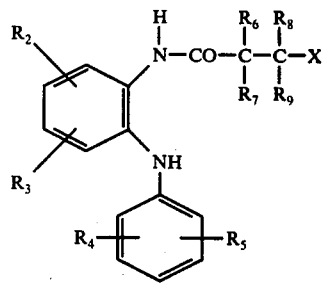

wherein X is halogen, with an alkali metal amide in liquid ammonia or with an alkali carbonate in a polar aprotic solvent at a temperature from 80° to 200° C., thereby directly to cyclize said amine.

2. A method as in claim 1 wherein the cyclized product is subsequently alkylated to replace hydrogen by lower alkyl, lower alkenyl, or lower alkinyl on the nitrogen atom in the 5-position.

3. The method as in claim 1 wherein said amine is reacted with sodium amide in liquid ammonia.

4. The method as in claim 1 wherein said amine is reacted with an alkali carbonate in dimethylformamide.

* * * * *